United States Patent
Wang et al.

(10) Patent No.: US 10,603,166 B2
(45) Date of Patent: Mar. 31, 2020

(54) DELIVERY DEVICE HAVING A CURVED SHAFT AND A STRAIGHTENING MEMBER FOR TRANSCATHETER AORTIC VALVE IMPLANTATION

(75) Inventors: Huisun Wang, Maple Grove, MN (US); Ralph Joseph Thomas, Champlin, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 324 days.

(21) Appl. No.: 13/823,415

(22) PCT Filed: Sep. 16, 2011

(86) PCT No.: PCT/US2011/001595
§ 371 (c)(1),
(2), (4) Date: Oct. 29, 2013

(87) PCT Pub. No.: WO2012/039748
PCT Pub. Date: Mar. 29, 2012

(65) Prior Publication Data
US 2014/0052238 A1  Feb. 20, 2014

Related U.S. Application Data

(60) Provisional application No. 61/384,549, filed on Sep. 20, 2010.

(51) Int. Cl.
*A61F 2/24* (2006.01)
*A61F 2/966* (2013.01)
(Continued)

(52) U.S. Cl.
CPC ............ *A61F 2/2436* (2013.01); *A61F 2/966* (2013.01); *A61F 2250/0018* (2013.01);
(Continued)

(58) Field of Classification Search
CPC ...... A61F 2/2436; A61F 2/2427; A61F 2/243; A61F 2/2433; A61F 2/2439;
(Continued)

(56) References Cited

U.S. PATENT DOCUMENTS

| 5,702,368 A | 12/1997 | Stevens et al. |
| 2004/0133264 A1* | 7/2004 | Moore ................ A61F 2/966 623/1.12 |

(Continued)

FOREIGN PATENT DOCUMENTS

| WO | 2011008812 A2 | 1/2011 |
| WO | 2011035327 A1 | 3/2011 |

(Continued)

OTHER PUBLICATIONS

International Search Report for Application No. PCT/US2011/001595 dated Apr. 16, 2012.

*Primary Examiner* — Katherine H Schwiker
(74) *Attorney, Agent, or Firm* — Lerner, David, Littenberg, Krumholz & Mentlik, LLP

(57) ABSTRACT

A delivery device may generally include a support member, a distal sheath, an outer shaft and a straightening member. The support member is adapted to hold a prosthetic heart valve. The distal sheath is slidable relative to the support member between a first position in which the distal sheath is adapted to maintain the prosthetic heart valve in a collapsed condition, and a second position in which the distal sheath is adapted to expose the prosthetic heart valve. The outer shaft is connected to the distal sheath and has a curved portion. The straightening member is slidable on the outer shaft between a proximal position in which the straightening member does not cover the curved portion of the outer shaft, and a distal position in which the straightening member
(Continued)

covers and substantially straightens at least a portion of the curved portion of the outer shaft.

10 Claims, 4 Drawing Sheets

(51) Int. Cl.
    *A61M 25/00*     (2006.01)
    *A61M 25/01*     (2006.01)

(52) U.S. Cl.
    CPC ............. *A61F 2250/0019* (2013.01); *A61F 2250/0029* (2013.01); *A61M 25/0041* (2013.01); *A61M 25/01* (2013.01); *A61M 2025/0004* (2013.01)

(58) Field of Classification Search
    CPC .......... A61F 2/2466; A61F 2/95; A61F 2/962; A61F 2/966; A61F 2/97; A61F 2250/0018; A61F 2250/0019; A61F 2250/0029; A61F 2/954; A61F 2002/9665; A61F 2002/9511; A61F 2002/9517; A61F 2002/9528; A61F 2002/9534; A61F 2/958; A61F 2002/9505; A61F 2002/9522; A61F 2002/9583; A61F 2002/9586; A61M 2025/0004; A61M 25/0041; A61M 25/0147; A61M 2025/0681; A61M 2025/0161; A61M 2025/0063; A61M 2025/015; A61M 2210/125; A61M 25/0133; A61M 25/0138; A61M 25/0141; A61M 25/0144; A61M 25/0152; A61M 25/0105; A61B 2017/00783; A71M 2025/0004

USPC ....................................................... 623/2.11
See application file for complete search history.

(56) References Cited

U.S. PATENT DOCUMENTS

| | | | |
|---|---|---|---|
| 2005/0148997 A1 | 7/2005 | Valley et al. | |
| 2005/0283223 A1* | 12/2005 | Greenan | A61F 2/95 623/1.11 |
| 2006/0167535 A1* | 7/2006 | Johnson | 607/122 |
| 2007/0135818 A1* | 6/2007 | Moore | A61F 2/07 606/108 |
| 2008/0097394 A1* | 4/2008 | Lampropoulos et al. | 604/524 |
| 2008/0264102 A1* | 10/2008 | Berra | A61F 2/07 63/1.11 |
| 2009/0048668 A1* | 2/2009 | Wilson et al. | 623/2.36 |
| 2010/0094257 A1* | 4/2010 | Stalker | A61M 25/0041 604/524 |
| 2010/0121341 A1* | 5/2010 | Devonec | A61F 2/04 606/108 |
| 2010/0312325 A1* | 12/2010 | Dorn | 623/1.13 |
| 2011/0251680 A1* | 10/2011 | Tran | A61F 2/2436 623/2.11 |
| 2011/0251683 A1* | 10/2011 | Tabor | A61F 2/2436 623/2.11 |
| 2012/0101563 A1* | 4/2012 | Zhu | A61F 2/954 623/1.12 |

FOREIGN PATENT DOCUMENTS

| | | |
|---|---|---|
| WO | 2011126749 A1 | 10/2011 |
| WO | 2012023980 A1 | 2/2012 |

* cited by examiner

DELIVERY DEVICE HAVING A CURVED SHAFT AND A STRAIGHTENING MEMBER FOR TRANSCATHETER AORTIC VALVE IMPLANTATION

CROSS-REFERENCE TO RELATED APPLICATIONS

This application is a national phase entry under 35 U.S.C. § 371 of International Application No. PCT/US2011/001595 filed Sep. 16, 2011, published in English, which claims the benefit of the filing date of U.S. Provisional Patent Application No. 61/384,549 filed Sep. 20, 2010, the disclosures of which are hereby incorporated herein by reference.

BACKGROUND OF THE INVENTION

The present disclosure relates to heart valve replacement and, more specifically, to devices and methods for implanting a collapsible prosthetic heart valve in a patient.

A healthy aortic valve acts as a one-way valve, opening to allow blood to flow out of the left ventricle of the heart, and then closing to prevent blood from flowing back into the heart. Diseased or damaged aortic valves may not close properly and thus allow blood to flow back into the heart. Damage to aortic valves may occur due to congenital defects, the natural aging process, infection or scarring. Diseased or damaged aortic valves sometimes need to be replaced to prevent heart failure. In such cases, collapsible prosthetic heart valves may be used to replace the native aortic valve.

Current collapsible prosthetic heart valve designs may be used in high-risk patients who may need a cardiac valve replacement, but who are not appropriate candidates for conventional open-chest, open-heart surgery. These collapsible and re-expandable prosthetic heart valves can be implanted transapically or percutaneously through the arterial system. One percutaneous delivery method entails introducing a collapsible prosthetic heart valve through a patient's femoral artery. This delivery method is referred to as a transfemoral approach.

A collapsible prosthetic heart valve may be delivered into a patient via a tube-like delivery apparatus such as a catheter, a trocar, a laparoscopic instrument, or the like. To place such a valve into a delivery apparatus and ultimately into a patient, the valve must first be collapsed or crimped to reduce its circumferential size. The delivery apparatus is then introduced transapically or percutaneously into a patient until it reaches the implant site.

When a collapsed heart valve has reached the desired implant site in the patient (e.g., at or near the annulus of the patient's heart valve that is to be replaced by the prosthetic valve), the prosthetic heart valve can be released from the delivery apparatus and re-expanded to its full operating size.

As stated above, collapsible prosthetic heart valves may be delivered to the valve annulus, and particularly the aortic valve annulus, either transfemorally or transapically. With either technique, however, it is difficult to properly align the collapsible heart valve with the valve annulus.

In transfemoral valve implantation, the collapsible prosthetic heart valve is delivered in a retrograde manner from the femoral artery through the aortic arch A to the native aortic valve annulus, as seen in FIG. 1. During delivery, the distal sheath 12 of the delivery device 10 is bent significantly to pass through the aortic arch A, which significantly biases the sheath toward the outside wall of the aortic arch. When the distal sheath passes through the aortic arch A and enters the left ventricle, it may exert a force on the septum wall S of the heart, as seen in FIG. 1. Depending on the bending angle of the aortic arch A and the stiffness of the outer shaft 14 of the delivery device 10, the distal sheath 12 may exert as much as 1 pound of force on the septum wall S of the heart. This excessive force could affect the electrical conduction system of the heart. For instance, an excessive force on the septum wall S of the heart may cause arrhythmic conditions (i.e., irregular cardiac rhythm), such as a ventricular fibrillation during the valve implantation or an atrioventricular block after implantation.

It is therefore desirable to reduce the force exerted on the septum wall S of the heart during valve implantation. To address this issue, the stiffness of the delivery catheter shaft could be decreased. However, reducing the stiffness of the delivery catheter shaft would likely sacrifice at least some of the columnar strength necessary for deployment and resheathing. Another possible solution is to employ a steerable catheter. Steerable catheters, however, can be bulky, expensive to make and more complicated to use. It is therefore desirable to have devices and methods which can effectively deliver and deploy a prosthetic heart valve without significantly changing the delivery device.

SUMMARY OF THE INVENTION

The present disclosure relates to delivery devices and methods for implanting a prosthetic heart valve. In one embodiment, the delivery device may generally include a support member, a distal sheath, an outer shaft and a strengthening member. The support member is adapted to hold a prosthetic heart valve. The distal sheath is slidable relative to the support member between a first position in which the distal sheath is adapted to maintain the prosthetic heart valve in a collapsed condition, and a second position in which the distal sheath is adapted to expose the prosthetic heart valve. The outer shaft is connected to the distal sheath and has a curved portion. The straightening member is slidable on the outer shaft between a proximal position in which the straightening member does not cover the curved portion of the outer shaft, and a distal position in which the straightening member covers and substantially straightens at least a portion of the curved portion of the outer shaft.

The straightening member may include a flexible portion and a substantially stiff portion. The flexible portion may be located proximally of the substantially stiff portion and may have a hardness of about 35 D. The substantially stiff portion of the straightening member may have a hardness of at least about 72 D. The straightening member may further include a hub positioned at a proximal end thereof. The flexible portion may extend between the hub and the substantially stiff portion of the straightening member. The curved portion of the outer shaft may have a radius of curvature of between about 2 inches and about 3 inches.

The delivery device may further include an outer tube operatively connected to the support member and extending through the outer shaft. The outer tube may have a curved portion adapted to lie within the curved portion of the outer shaft when the distal sheath is in the first position.

BRIEF DESCRIPTION OF THE DRAWINGS

Various embodiments of the present invention will now be described with reference to the appended drawings. It is appreciated that these drawings depict only some embodiments of the invention and are therefore not to be considered limiting of its scope.

DETAILED DESCRIPTION

Figure 1:
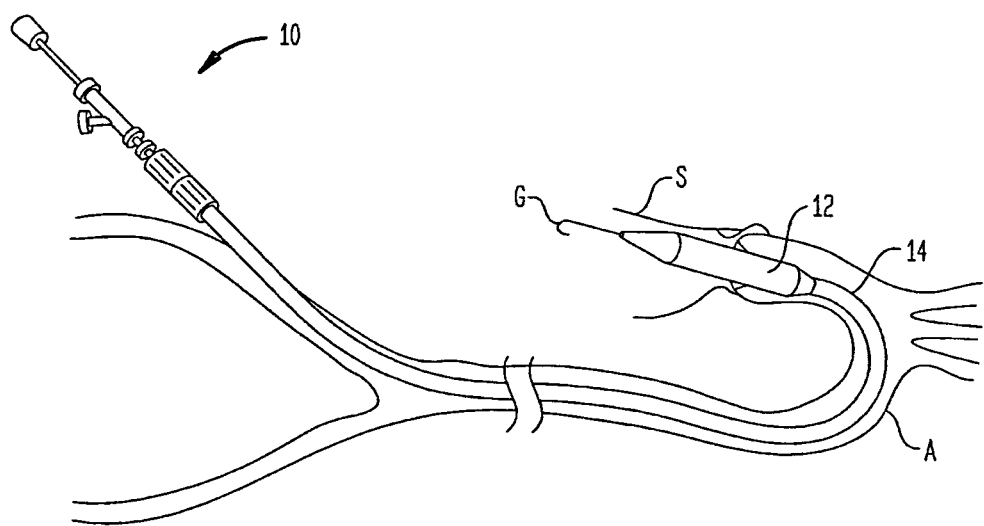
FIG. 1 is a side view of a conventional delivery device inserted through an aortic arch of a patient.

Embodiments of the presently disclosed delivery devices are described herein in detail with reference to the drawing figures, wherein like reference numerals identify similar or identical elements. In the drawings and in the description which follows, the term "proximal" refers to the end of the delivery device, or portion thereof, which is closest to the operator during use, while the term "distal" refers to the end of the delivery device, or portion thereof, which is farthest from the operator during use.

Figure 2:
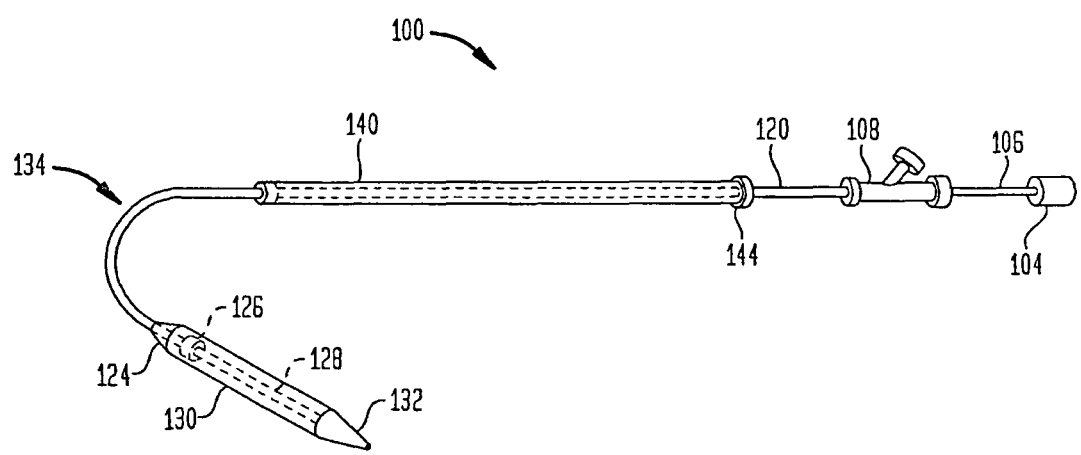
FIG. 2 is a side view of a delivery device according to an embodiment of the present invention having a straightening member in a proximal position and an outer shaft with a curved distal portion.

FIG. 2 illustrates a transfemoral delivery device 100 according to an embodiment of the present invention. The delivery device 100 may include an inner tube 106 having a lumen extending therethrough. A hub 104 mounted on the proximal end of the inner tube 106 is adapted for connection to another system or mechanism, such as a handle, a syringe or a mechanism for displacing the distal sheath 130. Mechanisms for displacing the distal sheath 130 are described in U.S. Provisional Patent Application No. 61/374,458, filed on Aug. 17, 2010, the entire contents of which are hereby incorporated herein by reference. At least a portion of the inner tube 106 extends through a Y-connector 108 and an outer shaft 120. The Y-connector 108 may include a hemostasis valve for preventing, or at least hindering, blood flow between the inner tube 106 and the outer shaft 120. In addition, the Y-connector 108 may be fluidly coupled to a fluid source.

The outer shaft 120 has a distal portion 134 that is deliberately curved to better accommodate the curve of the aortic arch and thereby minimize any structural damage to the arch or any impact on the electrical conduction system of the heart. At least a portion of the inner tube 106 extending through the distal curved portion 134 may also be deliberately curved and preferably has the same curvature as the distal curved portion 134. The distal curved portion 134 may be substantially resilient, and may extend to a tapered transition member 124 connected between the distal end of the outer shaft 120 and the distal sheath 130. The length of the distal curved portion 134 may be between about 2 inches and about 6 inches. The radius of curvature of the distal curved portion 134 may be between about 1 inch and about 3 inches. The distal curved portion 134 of the outer shaft 120 may be formed by subjecting a portion of a tube to a heating process suitable to cause the material of the tube to permanently deform to a new shape. Such method may include placing a portion of the tube over a curved mandrel, heating the tube, and allowing the tube to cool on the mandrel so as to assume the curved shape of the mandrel. Examples of suitable heating processes are described in U.S. Provisional Patent Application No. 61/374,458 filed on Aug. 17, 2010, the entire contents of which are incorporated herein by reference. As described in the aforementioned provisional patent application, the distal sheath 130 may also have a curved configuration.

Figure 5:
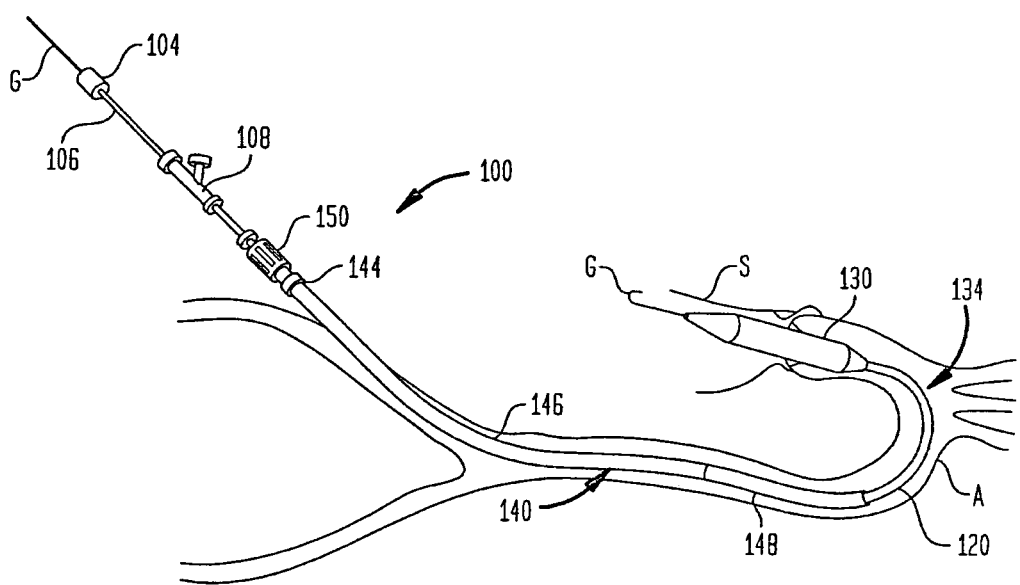
FIG. 5 is a side view of the delivery device shown in FIG. 2 inserted in an aortic arch of a patient.

The distal sheath 130 surrounds at least a portion of a support shaft 128 and can retain a prosthetic heart valve mounted around the support shaft in a collapsed condition. The support shaft 128 may be operatively connected to the inner tube 106 and may have a lumen extending therethrough for receiving a guidewire G, as seen in FIG. 5. A retaining element 126 mounted on the support shaft 128 is configured for supporting an end of a collapsible prosthetic heart valve or any other suitable medical implant. The retaining element 126 may be longitudinally and rotatably fixed relative to the support shaft 128, thereby preventing the stent portion of the collapsible heart valve from becoming tangled during delivery and deployment. The distal sheath 130 covers the retaining element 126 and at least a portion of the support shaft 128 and is movable relative to the support shaft between a distal position shown in FIG. 2 and a proximal position (not shown). A tip 132 may be connected to the distal end of the support shaft 128 and may have a tapered shape.

Figure 3:
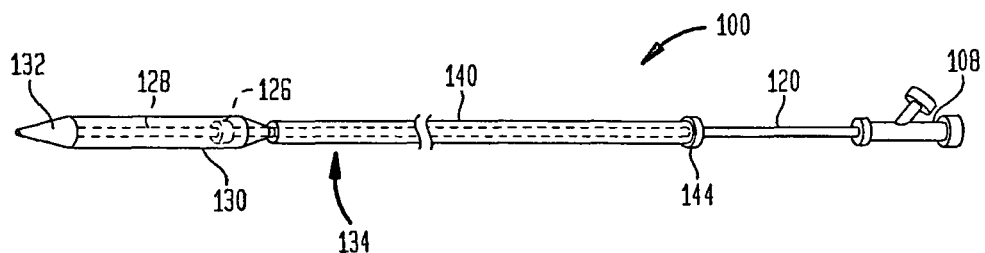
FIG. 3 is a side view of the delivery device of FIG. 2, depicting the straightening member in a distal position in which it covers and straightens the distal portion of the outer shaft.
Figure 4:
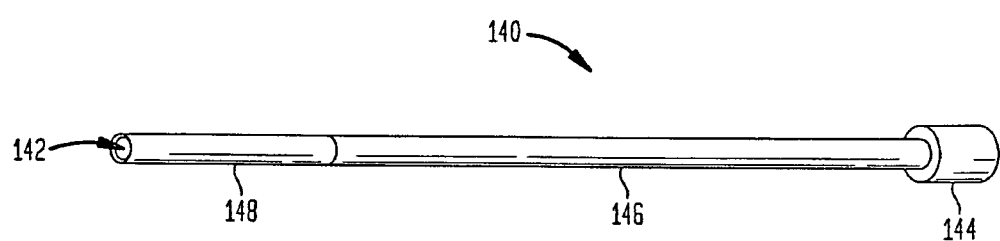
FIG. 4 is a perspective view of the straightening member of the delivery device shown in FIG. 2.

With reference to FIGS. 2-4, the delivery device 100 further includes a straightening or reinforcing member 140 made partly or entirely of a substantially stiff or rigid material. The straightening member 140 may have a substantially cylindrical shape and a lumen 142 extending therethrough. The straightening member 140 may have a length that is about the length of the portion of the outer shaft 120 not including the distal curved portion 134, and an inner diameter that is larger than the outer diameter of the outer shaft 120. As such, the straightening member 140 is slidable on the outer shaft 120 between a proximal position, shown in FIG. 2, and a distal position, shown in FIG. 3. As discussed in detail below, when slid to the distal position, the straightening member 140 can straighten the distal curved portion 134 of the outer shaft 120 (as well as any curved portion of the inner tube 106 extending therethrough). The delivery device 100 may be packed in a curved tray or a tray with a curved recess when delivered from the manufacturer to the end user, with the straightening member 140 in the proximal position, in order to maintain the distal curved portion 134 of the outer shaft 120 in a curved configuration.

FIG. 4 shows a straightening member 140 according to an embodiment of the present invention. In this exemplary embodiment, the straightening member 140 may include a hub 144 located at its proximal end. The hub 144 may be adapted for connection to a handle or a mechanism for displacing the straightening member 140 relative to the outer shaft 120 between the proximal and distal positions. The hub 144 of the straightening member 140 may have an outer diameter larger than the diameter of the remaining portions of the straightening member.

In addition to the hub 144, the straightening member 140 may include a section 148 located at its distal end and entirely or partly formed of any material that is suitably hard to render section 148 stiff. As used herein, the term "stiff" refers to the ability of section 148 to withstand any significant deformation by flexing when subjected to a bending force exerted by the presence of the distal curved portion 134 of the outer shaft 120 and the curved portion of inner tube 106 therein. In other words, section 148 is sufficiently stiff to substantially straighten the distal curved portion 134 of the outer shaft 120 and the curved portion of inner tube 106 when the straightening member 140 is in the distal position, as shown in FIG. 3. For example, section 148 of the straightening member 140 may have a hardness of at least about 72 D (shore durometer). In view of the relatively small lumen size of the patient's vasculature, it will be appreciated that it is preferable to form section 148 from a suitably hard material rather than increasing the stiffness of section 148 by increasing the wall thickness thereof. Examples of suitable hard materials include, but are not limited to, a 72 D polyether block amide sold under the trademark PEBAX® by Arkema France Corporation, polyetheretherketone (PEEK) and/or nylon-11 (polyamide 11).

Section 148 of the straightening member 140 may be sufficiently short to pass through the aortic arch A without much difficulty and sufficiently long to substantially straighten the distal curved portion 134 so as to be able to deliver device 100 through the patient's vasculature. For example, section 148 of the straightening member 140 may have a length between about 2 centimeters and about 7 centimeters.

The straightening member 140 may further include a flexible section 146 extending between the hub 144 and stiff section 148. The flexible section 146 is partly or entirely made of material which is more flexible than the material forming section 148. For example, the flexible section 146 of the straightening member 140 may be partly or entirely made of any suitable medium or low durometer material, including materials having a hardness of about 35 D. Examples of materials suitable for the flexible section 146 include, but are not limited to, a 35 D polyether block amide sold under the trademark PEBAX® by Arkema France Corporation and/or nylon-12 (polyamide 12). The flexible section 146 may additionally include braided metal or polymer wires to prevent it from kinking without sacrificing much flexibility. Regardless of its specific hardness, the flexible section 146 is sufficiently flexible to bend when passing through the curved passages of a patient's vasculature, such as the aortic arch.

In operation, the delivery device 100 may be used to implant a self-expanding prosthetic heart valve in a native valve annulus of a patient's heart. As seen in FIG. 5, the delivery device 100 may be inserted into the patient's vasculature using the transfemoral approach. In the transfemoral approach, the delivery device 100 is inserted in a retrograde manner from the femoral artery through the aortic arch A to the native aortic valve annulus.

Before inserting the delivery device 100 into the patient, the user may insert a guidewire G through the patient's vasculature until it reaches the desired site (i.e., the native valve annulus). The delivery device 100 may then be positioned over the guidewire G with the straightening member 140 in the distal position to substantially straighten the distal curved portion 134 and the distal sheath 130 also in the distal position. The delivery device 100 may be moved distally through the patient's vasculature until the distal curved portion 134 reaches the aortic arch A. The user may begin to retract the straightening member 140 proximally as he/she continues to advance the delivery device 100 distally through the aortic arch A to direct the distal sheath 130 toward the left ventricle of the patient's heart. As shown in FIG. 5, the user may retract straightening member 140 by manually moving the straightening member with respect to the outer shaft 120 through a handle or knob 150 connected to the hub 144. The partial retraction of the straightening member 140 will expose a segment of the distal curved portion 134, enabling it to relax to its curved configuration and better maneuver through the aortic arch without exerting excessive force on the outside wall thereof. As the distal sheath 130 of the delivery device 100 enters the left ventricle, the user may further retract the straightening member proximally so as to expose a greater extent of the distal curved portion 134 and cause the distal sheath 130 to move away from the septum wall S. At this juncture, the user may determine whether the distal sheath is aligned with the native valve annulus. If not so aligned, the user may move the straightening member 140 either proximally or distally to control the amount of section 148 thereof that covers the distal curved portion 134. Moving the straightening member 140 proximally will expose a greater amount of the distal curved portion 134, causing the distal sheath 130 to move in a direction away from the septum wall S. Alternatively, moving the straightening member 140 distally to expose less of the distal curved portion 134 will cause the distal sheath 130 to move toward the septum wall S.

With the distal sheath 130 spaced from the septum wall S and approximately aligned with the native valve annulus, the user may slide the distal sheath from the distal position to the proximal position to uncover the prosthetic heart valve supported on the support shaft 128 and therefore deploy the heart valve at or near the native valve annulus. Before completing deployment of the prosthetic heart valve, the user may determine if the prosthetic heart valve is located at the correct position. If no correction is necessary, the user may finish deploying the prosthetic heart valve. If a correction is necessary, the distal sheath 130 may be slid back to the distal position to again collapse the prosthetic heart valve, and the delivery device 100 may then be repositioned. Once the distal sheath 130, and more particularly, the heart valve within the distal sheath, is in the correct position, the user may slide the distal sheath 130 to the proximal position to deploy the prosthetic heart valve. With the heart valve deployed, the user may control the proximal and/or distal movement of the straightening member 140, and thus the exposed length of distal curved portion 134, in order to remove the delivery device 100 smoothly, without exerting excessive force on any of the patient's vasculature.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A delivery device for implanting a prosthetic heart valve in a native valve annulus of a patient, comprising:
   a support shaft adapted to hold a prosthetic heart valve in a position surrounding the support shaft;
   a distal sheath slidable relative to the support shaft between a first position in which the distal sheath covers the support shaft to maintain the prosthetic heart valve in a collapsed insertion condition, and a second position in which the distal sheath uncovers the support shaft to expose the prosthetic heart valve for deployment, the distal sheath having a predetermined outer diameter when inserted into the patient with the prosthetic heart valve in the collapsed insertion condition, the support shaft extending through the distal sheath in the first position;

an outer shaft connected to the distal sheath, the outer shaft having a first portion and a remainder, the first portion being biased to a first curved configuration and the remainder having a length;

an inner tube operatively connected to the support shaft and extending through the outer shaft, the inner tube having a distal portion biased to a second curved configuration, the distal portion being positioned within the first portion of the outer shaft when the distal sheath is in the first position; and a straightening member having a length substantially equal to the length of the remainder of the outer shaft and an inner diameter larger than an outer diameter of the outer shaft and smaller than the predetermined outer diameter of the distal sheath so that the distal sheath and the prosthetic heart valve in the collapsed insertion condition are not freely receivable within the straightening member, the straightening member having a flexible portion and a substantially stiff portion, the length of the straightening member being such that, when the straightening member is inserted into the patient using a transfemoral approach, a distal end of the straightening member is configured to be located in the aortic arch of the patient while a proximal end of the straightening member is located outside of the patient, the straightening member being slidable over the outer shaft between a distal position in which the substantially stiff portion of the straightening member covers the first portion of the outer shaft and substantially straightens the first portion of the outer shaft and the distal portion of the inner tube, and a proximal position in which the substantially stiff portion of the straightening member does not cover the first portion of the outer shaft, the straightening member being adapted to move from the distal position to the proximal position while a prosthetic heart valve is covered by the distal sheath, the movement of the straightening member controlling a degree of curvature of both the first portion of the outer shaft and the distal portion of the inner tube to align the distal sheath with the native valve annulus of the patient.

2. The delivery device of claim 1, wherein the flexible portion of the straightening member is located proximally of the substantially stiff portion.

3. The delivery device of claim 1, wherein the flexible portion of the straightening member has a hardness of 35D.

4. The delivery device of claim 1, wherein the substantially stiff portion of the straightening member has a hardness of at least 72D.

5. The delivery device of claim 1, wherein the straightening member includes a hub positioned at the proximal end thereof.

6. The delivery device of claim 5, wherein the flexible portion extends between the hub and the substantially stiff portion of the straightening member.

7. The delivery device of claim 5, wherein the hub has an outer diameter that is larger than outer diameters of the flexible portion and the substantially stiff portion.

8. The delivery device of claim 1, wherein the first portion of the outer shaft is biased to a radius of curvature of between 2 inches and 3 inches.

9. The delivery device of claim 1, wherein the substantially stiff portion has a length between 2 cm and 7 cm.

10. The delivery device of claim 1, further comprising a tapered tip connected to a distal end of the support shaft.

* * * * *